United States Patent [19]

Hill

[11] Patent Number: 5,070,019

[45] Date of Patent: Dec. 3, 1991

[54] IMMOBILIZATION OF YEAST IN ALGINATE BEADS FOR PRODUCTION OF ALCOHOLIC BEVERAGES

[75] Inventor: Frank Hill, Mettmann-Oberschwarzbach, Fed. Rep. of Germany

[73] Assignee: Huels Aktiengesellschaft, Marl, Fed. Rep. of Germany

[21] Appl. No.: 489,535

[22] Filed: Mar. 7, 1990

[30] Foreign Application Priority Data

Mar. 18, 1989 [DE] Fed. Rep. of Germany ....... 3908997

[51] Int. Cl.$^5$ ............... C12N 11/10; C12N 11/04; C12C 11/00; C12G 1/00
[52] U.S. Cl. .................................... 435/178; 426/11; 426/15; 426/16; 426/62; 435/182
[58] Field of Search ............... 435/174, 177, 178, 182; 426/11, 15, 16, 62

[56] References Cited

U.S. PATENT DOCUMENTS

| | | | |
|---|---|---|---|
| 4,352,883 | 10/1982 | Lim | 435/178 |
| 4,524,137 | 6/1985 | Hagerdal et al. | 435/178 |
| 4,659,662 | 4/1987 | Hsu | 435/178 X |
| 4,663,286 | 5/1987 | Tsang et al. | 435/178 |
| 4,950,600 | 8/1990 | Tanaka et al. | 435/178 |

FOREIGN PATENT DOCUMENTS 0065376 11/1982 European Pat. Off. .

*Primary Examiner*—David M. Haff
*Attorney, Agent, or Firm*—Oblon, Spivak, McClelland, Maier & Neustadt

[57] ABSTRACT

Immobilized yeast for the production of alcoholic beverages is produced by forming calcium alginate beads containing yeast, hardening the beads for 30 to 180 minutes in a CaCl$_2$ solution, washing the beads for 100 to 500 minutes at 5° to 35° C. with water which may have a salt content of up to 0.5 g/l and drying the beads at a temperature of 10° to 50° C. The immobilized yeast is particularly suitable for use in the bottle fermentation of sparkling wine.

16 Claims, No Drawings

IMMOBILIZATION OF YEAST IN ALGINATE BEADS FOR PRODUCTION OF ALCOHOLIC BEVERAGES

BACKGROUND OF THE INVENTION

1. Field of the Invention

The present invention relates to a process for the preparation of yeast immobilized in alginate beads, immobilized yeast prepared by such process, and a method of preparing fermented liquids using such immobilized yeast.

2. Discussion of the Background

For the preparation of alcoholic drinks, such as, for example, beer, wine or sparkling wine, fermentation is carried out with the aid of yeast. When the fermentation is complete, the yeast must be removed completely to avoid cloudiness of the drinks.

Sparkling wine is prepared by means of a second fermentation of wine to which sugar and particular yeast strains have been added. The fermentation of sparkling wine takes place either in the commercially available champagne bottles, in larger special bottles or in steel tanks. In the case of fermentation in bottles, removing the yeast when the fermentation is complete is complicated. The bottle is stored in an inclined position and shaken repeatedly over a substantial period until the yeast sediments have deposited in the bottle neck. The bottle neck is cooled, during which process the sparkling wine together with the yeast freezes. The bottle is then opened, and the ice plug containing the yeast sediment is squeezed out of the bottle by the internal pressure.

According to FR 2,432,045, above-described process can be simplified. In FR 2,432,045, yeast cells which are enclosed in a calcium alginate gel and which deposit in the bottle neck without shaking are used.

According to EP-A-0,173,915, yeast cells for the production of sparkling wine are immobilized in alginate beads, after which the beads are coated with a cell-free calcium alginate layer, with the intent to ensure that no yeast cells are freed from the immobilisate.

DE-C-2,835,875 describes a complicated process for the preparation of pressure-resistant biocatalysts. Among others in this process, alginate beads containing yeast cells are solidified, washed with a physiological solution of sodium chloride, dried, shrunk and hardened. However, no mention is made in this publication of the production of sparkling wine.

Thus, if champagne yeasts are immobilized in calcium alginate, either no precautions are taken, or complicated measures are taken to avoid the dullness caused by liberated yeast cells. Accordingly, there remains a need for a simplified process for preparing immobilized yeast, which has good settling properties, and does not result in the escape of the yeast from the immobilisate; and the immobilized yeast prepared by such a process. There is also a need for a method of producing fermented liquids utilizing such immobilized yeast.

SUMMARY OF THE INVENTION

Accordingly, it is an object the present invention to provide a simplified process for the preparation of yeasts immobilized in alginate.

It is another object of the present invention to provide immobilized yeast which is suitable for the production of alcoholic drinks.

It is another object of the present invention to provide immobilized yeast which can be used in the bottle fermentation of sparkling wine without the occurrence of dullness.

These and other objects, which will become apparent during the following detailed description, have been achieved according to the invention by hardening calcium alginate beads in which yeast is immobilized for 30 to 180 minutes in a $CaCl_2$ solution, followed by washing for 100 to 500 minutes at 5° to 35° C. with water which may have a salt content of up to 0.5 g/l and then drying at 10° to 50° C. bulk temperature, to obtain immobilized yeast; and the use of such yeast in the production of fermented liquids.

DETAILED DESCRIPTION OF THE PREFERRED EMBODIMENTS

For the preparation of the yeast-containing calcium alginate beads, a 0.5 to 5 wt. %, preferably 1 to 4 wt. %, strength sodium alginate solution is usually employed in which the yeast is suspended. This suspension is then added dropwise to a precipitation bath, which, in general, is a 0.5 to 20 wt. %, preferably 2 to 15 wt. %, strength $CaCl_2$ solution. This gives beads or granules with diameters of 1 to 6 mm.

The biomass content of the beads prepared according to the present invention is usually in the range of 15 to 80 wt. %, preferably 25 to 70 wt. %, and the alginate content is about 80 to 15 wt. %, preferably 70 to 25 wt. %. The residual moisture is 5 to 20%.

Yeasts which are suitable for the production of sparkling wine include, for example, *Saccharomyces bayanus* or *Saccharomyces cerevisiae*.

The beads usually are kept in the precipitation bath until they have hardened, whereupon they are removed in the moist state and washed with a sufficient amount of water. Washing can be effected in a flask or vat, with shaking or stirring. This process usually involves the use of a 10 to 300 fold excess of water, based on the weight of the moist beads. When a smaller excess is used, the washing step is not always successful. Admittedly, the washing step can also be effected using a more than 300 fold excess, but such excessive amounts are unnecessary and uneconomical It is also possible to effect washing under running water.

The washing time is suitably 100 to 500 minutes, preferably 120 to 300 minutes. Washing is suitably effected at a temperature of 5° to 35° C., preferably 10° to 30° C.

The water employed for washing is virtually sterile, such as, for example, tap water, mineral water, partly demineralized water and deionized water. Washing is preferably effected with with deionized water. The salt content of the water is suitably up to 0.5 g/l preferably up to 0.25 g/l.

Drying, which is suitably carried out at a temperature of 10° to 50° C., preferably 15° to 40° C., of the beads, can be carried out, for example, in a circulating-air oven or in a fluidized bed. Pre-dried air can also be used for this process.

It is preferred to effect drying up to a dry matter content of 80 to 95%.

The resulting alginate beads containing yeast are highly suitable for the fermentation of alcoholic drinks, such as, for example, beer, wine or sparkling wine. The production of such alcoholic beverages can be achieved by fermenting a suitable fermentable starting material in the conventional manner. The fermentable starting materials and fermentation methods for these alcoholic beverages are well known in the art (see, e.g., Kirk-Othmer, Encyclopedia of Chemical Technology, Vol. 3, pp. 693–735 and Vol. 24, pp. 549–578, Wiley (1984), incorporated herein by reference). After the fermentation, the beads and hence also the yeast can be removed quantitatively in a simple manner by decanting or filtration. Thus, the drinks remain clear.

The calcium alginate beads prepared according to the present invention, in which champagne yeast is immobilized, can still be employed for the production of sparkling wine after several months storage, if they are stored under cool and dry conditions. For the fermentation of sparkling wine, about 0.2 to 2 g of dried beads are employed per 1 liter of original wine to which sugar has been added. At 20° C., the fermentation of sparkling wine is complete in 3 to 8 weeks.

A suitable starting or original wine is, above all, a wine containing up to 10 g of free acid per liter, expressed as tartaric acid. With this acid content, the sparkling wine remains clear after the fermentation. There is neither a crystalline precipitate nor cloudiness formed by yeast cells.

The calcium alginate beads prepared by the process according to the present invention have a content of leachable calcium of 0.9 to 1.6 mg of Ca/g of beads, preferably 1.0 to 1.5 mg/g.

When the washing step is not effected long enough, the content of leachable calcium is too high, so that cloudiness, caused mainly by the formation of crystals (calcium tartrate and calcium malate) occurs, or may occur, during the fermentation of sparkling wine. When the content of leachable calcium is too low, the network is no longer dense enough, so that dullness of the wine, caused by liberated and multiplying cells which have unfavorable sedimentation qualities, occurs.

The process according to the present invention, in contrast, provides an immobilisate in a simple manner, which can be used for the fermentation of sparkling wine during which neither turbidity caused by crystals nor cloudiness caused by yeast cells occurs, and in which it is therefore assured that the sparkling wine remains clear.

Other features of the invention will become apparent in the course of the following descriptions of exemplary embodiments which are given for illustration of the invention and are not intended to be limiting thereof.

EXAMPLES

In the examples which follow, the Examples according to the invention are identified by numbers and the Comparative Examples by letters.

Preparation and hardening of the calcium alginate beads 5 g of sodium alginate (PROTANAL$^R$ LF 20/60, manufactured by Protan, D-2000 Hamburg) are sprinkled in to 100 ml of drinking water. The stirred batch is heated to 90° C. The temperature is maintained at 90° C. for 1 hour, during which process the sodium alginate dissolves. After the solution has cooled to 35° C., 120 g of a suspension of freshly prepared yeast cells of the strain *Saccharomyces bayanus* (dry matter content 5%) are added. The resulting mixture contains 45% of alginate and 55% of biomass, based on the total dry matter content.

The suspension which is free from lumps is transferred to a pressurized vessel whose bottom is equipped with 32 jet needles of 0.5 mm internal diameter. The suspension is pressed through the jet needles at a pressure of about 1.5 bar. The drops which are detached from the jet needles fall into 600 ml of a slightly stirred 2% strength $CaCl_2$ solution from a height of about 10 cm.

After the suspension has been pressed through the jet needles for 10 minutes, the beads which have formed remain in the precipitation bath for another hour for hardening, with slight stirring.

Washing and drying

The moist beads which are formed are isolated by sieving, rinsed for 20 seconds with tap water and then seven 100 g portions of these beads are added to 10 liters of deionized water in each case, whereby they are washed for the time period specified in Table I, with slight stirring.

The moist beads which have a diameter of about 2.5 mm and a dry matter content of 8% are isolated by sieving and dried by fluidized bed drying in a glass tube having a fritted bottom. The air used for this process is preheated to 50° C. The drying step is finished when the product temperature has increased to 35° C. The beads then have a dry matter content of 85 to 88% and have shrunk to a diameter of about 0.8 mm. Compared with the moist cells, the fermentation activity is reduced to 30 to 50%.

The following tests are carried out using the thus-obtained samples:

(a) Content of water-leachable $Ca^{++}$ 1 g of dry granules (beads) is allowed to stand for 24 hours in 5 ml of deionized water. The supernatant is subsequently decanted and the content of $Ca^{++}$ which dissolved in the water is determined.

(b) Formation of calcium tartrate/calcium malate in the original wine and in the acidified original wine 100 ml of a dry white wine (7.9% ethanol, 0.2% glucose, 0.47% malic acid, 0.18% L-tartaric acid, pH 3.2) or of an acidified original wine which is prepared from the above white wine by the addition of solid L-tartaric acid and which has a tartaric acid content of 0.73%, are treated with 1 g of dry yeast immobilisate, and the mixture is then allowed to stand in a sealed vessel for 3 weeks at 20° C.

Using a magnifying glass, the immobilisate is then examined for growth of crystals on the surface.

The results for tests (a) and (b) as a function of the duration of washing are shown in Table I.

TABLE I

| Example | Duration of washing [min] | Leachable $Ca^{++}$ from the dried granules [mg/g] | Growth of crystals original wine | Growth of crystals acidified original wine |
|---------|---------------------------|----------------------------------------------------|----------------------------------|--------------------------------------------|
| A | 10 | 2.8 | + | + |
| B | 30 | 2.0 | (+) | + |
| C | 60 | 1.8 | − | (+) |
| 1 | 120 | 1.5 | − | − |
| 2 | 240 | 1.3 | − | − |
| 3 | 360 | 1.1 | − | − |
| D | 600 | 0.7 | − | − |

+: substantial amount of crystals
(+): minor amounts of crystals
−: no crystals c) Fermentation of sparkling wine 24 g/l of saccharose are dissolved in a dry white wine having the above characteristics. Batches of 0.7 liters of this wine to which sugar has been added are filled into three pressure-stable bottles, whereupon 1.5 g of champagne yeast immobilisate according to Comparative Example A, Example 1, or Comparative Example D, are added.

The bottles are tightly sealed with corks and then stored horizontally at room temperature. After 4 weeks, the bottles are cooled to 4° C. and opened. The contents of the bottles are examined, and the results are shown in Table II.

TABLE II

| Immobi-lisate of Example | Immobilisate after the fermentation | Sugar content in the sparkling wine [g/l] | Flavor of the sparkling wine | Other remarks |
| --- | --- | --- | --- | --- |
| A | fused by crystal bridges to form solid mass | 2.0 | dry, without fault | cloudiness caused by crystals |
| 1 | particulate | 1.5 | dry, without fault | clear |
| D | particulate | 4.8 | virtually dry, without fault | slightly cloudy caused by yeast cells |

According to Table I, no growth of crystals on the immobilisate is observed in Examples 1 to 3 and in Comparative Example D. From Table II it is seen that a faultless sparkling wine is produced with the immobilisate of Example 1, but not with that of Comparative Example D.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by letters patent of the United States is:

1. A process for preparing yeast immobilized in calcium alginate beads which is useful for the production of alcoholic beverages, comprising the steps:
   (i) adding a sodium alginate solution containing yeast cells dropwise to a CaCl₂ solution, to obtain beads;
   (ii) hardening said beads in said CaCl₂ solution, for 30 to 180 minutes, to obtain hardened beads;
   (iii) washing said hardened beads for 100 to 500 minutes at 5° to 35° C. with water having a salt content of up to 0.5 g/l, to obtain washed beads; and
   (iv) drying said washed beads at a bead temperature of 10° to 50° C.

2. The process of claim 1, wherein said washing is carried out for 120 to 300 minutes at 10° to 30° C.

3. The process of claim 2, wherein said washing is carried out using deionized water.

4. The process of claim 1, wherein said drying is carried out at 15° to 40° C.

5. The process of claim 1, wherein said drying is carried out up to a dry matter content of 80 to 95 wt. %.

6. The process of claim 1, wherein said sodium alginate solution is a 0.5 to 5 wt. % sodium alginate solution.

7. The process of claim 1, wherein said CaCl₂ solution is a 0.5 to 20 wt. % CaCl₂ solution.

8. The process of claim 1, wherein said yeast is selected from the group consisting of *Saccharomyces bayanus* and *Saccharomyces cerevisiae*.

9. An immobilized yeast useful in the preparation of alcoholic beverages, prepared by a process comprising the steps of:
   (i) adding a sodium alginate solution containing yeast cells dropwise to a CaCl₂ solution to obtain beads;
   (ii) hardening said beads in said CaCl₂ solution, for 30 to 180 minutes, to obtain hardened beads;
   (iii) washing said hardened beads for 100 to 500 minutes at 5° to 35° C. with water having a salt content of up to 0.5 g/l, to obtain washed beads; and
   (iv) drying said washed beads at a bead temperature of 10° to 50° C.

10. The immobilized yeast of claim 9, wherein said washing is carried out for 120 to 300 minutes at 10° to 30° C.

11. The immobilized yeast of claim 10, wherein said washing is carried out using deionized water.

12. The immobilized yeast of claim 9, wherein said drying is carried out at 15° to 40° C.

13. The immobilized yeast of claim 9, wherein said drying is carried out up to a dry matter content of 80 to 95 wt. %.

14. The immobilized yeast of claim 9, wherein said sodium alginate solution is a 0.5 to 5 wt. % sodium alginate solution.

15. The immobilized yeast of claim 9, wherein said CaCl₂ solution is a 0.5 to 20 wt. % CaCl₂ solution.

16. The immobilized yeast of claim 9, wherein said yeast is selected from the group consisting of *Saccharomyces bayanus* and *Saccharomyces cerevisiae*.

* * * * *